US006432136B1

(12) United States Patent
Weiss et al.

(10) Patent No.: US 6,432,136 B1
(45) Date of Patent: Aug. 13, 2002

(54) APPARATUS AND METHOD FOR REMOVING A POCKET OF AIR FROM A BLOOD PUMP

(75) Inventors: William J. Weiss, Mechanicsburg; Marjorie Rawhouser, Palmyra, both of PA (US)

(73) Assignee: The Penn State Research Foundation, University Park, PA (US)

( * ) Notice: Subject to any disclaimer, the term of this patent is extended or adjusted under 35 U.S.C. 154(b) by 0 days.

(21) Appl. No.: 09/558,075

(22) Filed: Apr. 25, 2000

(51) Int. Cl.[7] .............................. A61M 1/12; G01B 7/14
(52) U.S. Cl. ................ 623/3.1; 324/207.2; 324/207.26; 623/913
(58) Field of Search ......................... 446/131, 133–135; 623/3.1, 3.28, 912, 913

(56) References Cited

U.S. PATENT DOCUMENTS

| | | |
|---|---|---|
| 3,043,309 A | 7/1962 | McCarthy |
| 3,674,014 A | 7/1972 | Tillander |
| 4,431,005 A | 2/1984 | McCormick |
| 4,771,237 A | 9/1988 | Daley |
| 4,905,698 A | 3/1990 | Strohl, Jr. et al. |
| 4,943,770 A | 7/1990 | Ashley-Rollman et al. |
| 5,257,636 A | 11/1993 | White |
| 5,316,024 A | 5/1994 | Hirschi et al. |
| 5,425,367 A | 6/1995 | Shapiro et al. |
| 5,425,382 A | 6/1995 | Golden et al. |
| 5,464,023 A | 11/1995 | Viera |
| 5,606,980 A | 3/1997 | Calhoun et al. |
| 5,674,281 A | 10/1997 | Snyder |
| 5,681,260 A | * 10/1997 | Ueda et al. .................. 600/114 |
| 5,727,553 A | 3/1998 | Saad |
| 5,751,125 A | 5/1998 | Weiss |
| 5,776,080 A | 7/1998 | Thome et al. |
| 5,906,579 A | * 5/1999 | Vander Salm et al. ...... 600/424 |

OTHER PUBLICATIONS

Internet web page (one page) from Panametrics NDT with Magna Mike Thickness Gage at http://panametrics.com/ndt/thickness/mm8000item.shtml, dated Jan. 8, 1997, downloaded Feb. 24, 1998.
Internet web page (three pages) from Panametrics NDT with Magna–Mike Model 8000 at http://www.panametrics.com/ndt/thickness/mm8000.shtml, downloaded Feb. 24, 1998.
Brochure for the Magna–Mike Model 8000 from Panametrics, Inc. dated Mar. 1996 (3 pages).
Internet web page (two pages) from Panametrics NDT with Ultrasonic Thickness Gauges at http://www.panametrics.com/ndt/thickness/index.shtml, downloaded Feb. 24, 1998.
Internet web page (two pages) from Panametrics NDT with information about Panametrics at http://www.ndt.net/exhibit/cust_sh/pan_sh1.htm, downloaded Feb. 24, 1998.

* cited by examiner

Primary Examiner—David H. Willse
(74) Attorney, Agent, or Firm—Marshall, Gerstein & Borun.

(57) ABSTRACT

A catheter having a first magnet is guided into a pocket of air entrapped in a pumping chamber for an artificial heart using a probe having a second magnet, a Hall-effect sensor an electronic circuit and an indicator disposed thereon. The Hall-effect sensor generates a voltage signal that is related to the distance between the catheter tip and the probe tip and that is measured by the electronic circuit and thereafter used to actuate the indicator. The indicator indicates when the probe is close enough to the catheter such that the catheter tip has been magnetically captured by the probe tip. Once magnetically captured, the probe tip, while remaining outside of the pumping chamber, is used to guide the catheter tip to an elevated portion of the pumping chamber wherein the pocket of entrapped air is located. A vacuum generating device attached to a distal end of the catheter tube is then used to withdraw the air from the pumping chamber.

23 Claims, 7 Drawing Sheets

| LED SEGMENT (202) | V_HS CONVERTED TO A DIGITAL VALUE (204) |
|---|---|
| 1 | 0 |
| 2 | 42 |
| 3 | 44 |
| 4 | 46 |
| 5 | 49 |
| 6 | 58 |
| 7 | 63 |
| 8 | 70 |
| 9 | 75 |
| 10 | 92 |
| 11 | 115 |

ANALOG VOLTAGE SIGNALS FOR $V_{HS}$ 0.0
0.82
0.86
0.90
0.96
1.13
1.23
1.37
1.46
1.80
2.25

201

APPARATUS AND METHOD FOR REMOVING A POCKET OF AIR FROM A BLOOD PUMP

This patent is subject to Government Contract No. N01-HV-38130 with the National Institutes of Health.

BACKGROUND OF THE INVENTION

The present invention is directed to a method and apparatus for removing a pocket of air from an inner chamber of an artificial heart assembly using a magnetically guided catheter.

After implantation of a blood pump, such as a total artificial heart or a ventricular assist device, into a recipient, the pump is filled with blood. While the pump is filling with blood, a pocket of air may become entrapped in a pumping chamber of the pump. The pocket of entrapped air must be removed before the pump is turned on to prevent the circulation of air bubbles in the blood stream which might otherwise lead to the death or stroke of the blood pump recipient.

A number of methods/devices are currently used to remove such a pocket of air from a blood pump. In one such method, the pump is tilted or manipulated to move the air out of the pumping chamber and into one or more connecting tubes that feed into the pumping chamber where the air is then withdrawn with a vacuum generator such as a syringe. In another such method, used with pumping chambers that are translucent such that the pocket of air can be visually located through a wall of the chamber, a catheter is threaded through an atrial suture line, then through an inlet valve and finally into the pump. Viewing the catheter tip through the pump chamber, the catheter tip is manipulated into the air pocket, and the air is then withdrawn using a vacuum generator attached to an opposing end of the catheter.

However, the method of tilting or otherwise manipulating the pumping chamber is not always possible because in some applications the implanted pump is not freely manipulable. The method of visually locating the catheter tip in the pocket of air is not always viable either because some blood pumps are opaque such that visually-aided positioning of the catheter is not possible.

Thus, there exists a need in the art for a method and apparatus for removing a pocket of air from an implanted blood pump that is not freely manipulable and that has opaque walls.

SUMMARY OF THE INVENTION

In one aspect, the invention is directed to a system for removing a pocket of gas from a blood pump having a wall portion with an inner surface and an outer surface and a chamber at least partially defined by the wall portion having a pocket of gas disposed therein; a catheter having a first attractive material that generates a first attractive field; a vacuum generator coupled to the catheter and being adapted to remove the pocket of gas from the chamber when a portion of the catheter is disposed therein; a positioning probe adapted to be disposed at a location outside of the chamber to allow the portion of the catheter to be positioned within the pocket of gas; a second attractive material associated with the probe, movement of the second attractive material causing movement of the first attractive material when the second attractive material is disposed outside the chamber and when the first attractive material is disposed within the chamber; a sensor associated with the probe, the sensor generating a proximity signal having a magnitude relating to a distance between the first attractive material and the second attractive material; an electronic circuit operatively coupled to the sensor, the electronic circuit generating an indicator signal in response to the proximity signal generated by the sensor; and an indicator operatively coupled to the electronic circuit, the indicator generating an indication based on the indicator signal generated by the electronic circuit, the indication relating to the distance between the first and second attractive materials.

In another aspect, the invention is directed to a method of removing gas from a pocket of gas disposed within a chamber of a blood pump using a catheter provided with a first material, the chamber of the blood pump being at least partially bounded by a wall portion and the pocket of gas being located adjacent an inner surface of the wall portion at least partially bounding the chamber of the blood pump, with the method comprising: a) disposing the catheter in the chamber of the blood pump; b) disposing a probe having a second material that attracts the first material of the catheter at a position in which the wall portion at least partially bounding the chamber of the blood pump is disposed between the first material of the catheter and the probe; c) monitoring an indicator to determine if the second material of the probe has attracted the first material of the catheter to a position disposed adjacent the inner surface of the wall portion at least partially bounding the chamber of the blood pump; d) moving the probe to cause the first material of the catheter to be moved so that the catheter is disposed in the pocket of gas; and e) with the catheter disposed in the pocket of gas in the chamber of the blood pump, operating a vacuum generator to cause gas to be removed from the chamber of the blood pump.

The features and advantages of the present invention will be apparent to those of ordinary skill in the art in view of the detailed description of the preferred embodiment, which is made with reference to the drawings, a brief description of which is provided below.

DETAILED DESCRIPTION OF THE PREFERRED EMBODIMENTS

Figure 1:
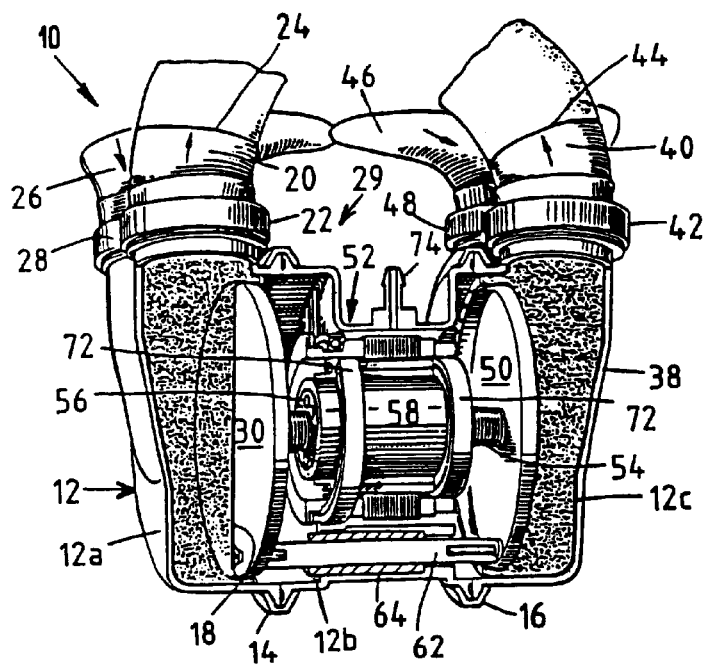
FIG. 1 is a perspective view of an artificial heart having an opaque pumping chamber, portions of which are shown in cross section.

FIG. 1 illustrates an artificial heart assembly 10 intended to be completely implanted within a recipient, such as a human or an animal, to take the place of, or assist, the recipient's natural heart. As defined herein, an artificial heart assembly intended for use with a recipient, such as an animal or human, may be a total artificial heart (TAH) intended to replace the entire heart of the recipient, or a ventricular assist device (VAD) intended to replace a portion of the recipient's heart.

The artificial heart 10 has a housing 12 composed of three sections 12a, 12b, 12c which are held together by a pair of annular V-rings 14, 16. A blood reservoir within a sac 18 disposed within the housing section 12a may be fluidly coupled to a blood outlet 20 defined by an artificial vascular graft connected to the housing section 12a via a threaded connector 22. The graft 20 may be connected to the pulmonary artery of the recipient via a suture line 24. The blood reservoir within the sac 18 may be fluidly coupled to a blood inlet chamber defined by an artificial graft 26 which may be connected to the housing section 12a via a threaded connector 28 and to the right atrium of the recipient via a suture line (not shown). A pair of one-way check valves (not shown) may be disposed in the blood inlet 26 and the blood outlet 20 to ensure that blood is pumped in the direction shown by the arrows in FIG. 1.

A blood sac 38 disposed within the housing section 12c may be fluidly coupled to a blood outlet 40 defined by an artificial graft connected to the housing section 12c via a threaded connector 42. The graft 40 may be connected to the aorta of the recipient via a suture line 44. The blood reservoir in the blood sac 38 may be coupled to a blood inlet chamber defined by an artificial graft 46 which is connected to the housing section 12c via a threaded connector 48 and to the left atrium of the recipient via a suture line (not shown). A pair of one-way check valves (not shown) may be disposed in the blood inlet 46 and the blood outlet 40 to ensure that blood is pumped in the direction shown by the arrows.

A pumping mechanism or pump 29 may be provided to pump blood from the blood inlet 26 to the blood outlet 20 and from the blood inlet 46 to the blood outlet 40. The pumping mechanism 29 has a pumping structure and a motor operatively coupled to drive the pumping structure. The pumping structure may be provided, for example, in the form of a pusher plate 30 that makes contact with and periodically deforms the blood sac 18 to force blood from the blood inlet 26 to the blood outlet 20 and a pusher plate 50 that makes contact with and periodically deforms the blood sac 38 to force blood from the blood inlet 46 to the blood outlet 40.

The pump 29 may include a DC brushless motor 52 that drives the pusher plates 30, 50 laterally back and forth. The motor 52 may be coupled to the pusher plates 30, 50 via a drive screw 54 and a coupling mechanism composed of a plurality of threaded elongate rollers 56 disposed within a cylindrical nut 58 fixed to a rotor (not shown) of the motor 52. Rotation of the rotor causes the nut 58 and rollers 56 to rotate, thus causing the drive screw 54 to be linearly displaced in a direction parallel to its longitudinal central axis. A guide rod 62 may be connected between the two pusher plates 30, 50 to pass through a fixed bushing 64 to prevent the plates 30, 50 from rotating. Other mechanisms for coupling the rotor to the pusher plates 30, 50 could be used.

The rotation of the rotor may be controlled via the electrical energization of a plurality of windings of a stator (not shown) which is rotatably coupled to the rotor via a pair of cylindrical bearings 72. A wire port 74 may. be formed in the housing section 12b to allow the passage of wires from the windings to a controller (not shown), which may be implanted in another area of the recipient, such as in the recipient's abdomen.

The structural details of the artificial heart 10 and the pumping mechanism 29 described above are exemplary only and are not considered important to the invention. Alternative designs could be utilized without departing from the invention.

Figure 2:
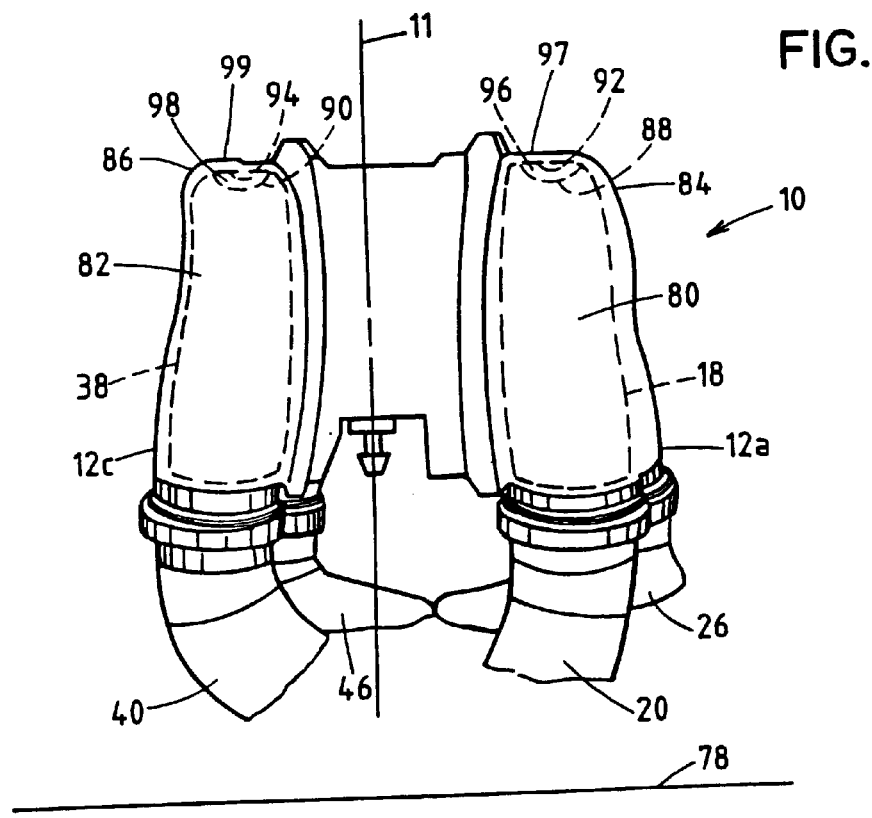
FIG. 2 illustrates the artificial heart rotated approximately one hundred and eighty degrees from the position occupied by the artificial heart in FIG. 1, wherein a pocket of air is located within the opaque pumping chamber and is disposed adjacent to a wall portion of the pumping chamber.

Referring now to FIG. 2, when the artificial heart 10 is implanted, the heart recipient (not shown) may be lying, for example, on his back on an operating table 78. Due to the anatomy and position of the recipient, when the artificial heart 10 is implanted, it is disposed in a position that is rotated approximately 180° from the position of the artificial heart 10 shown in FIG. 1 and is further positioned such that the center line 11 of the heart 10 is generally perpendicular to the operating table 78.

Each of the sacs 18, 38, together with the respective housings 12a, 12c within which the sacs 18, 38 are disposed, form a pumping chamber 80, 82, respectively, through which blood is pumped as it enters and exits the artificial heart 10. Each of the pumping chambers 80, 82 is at least partially defined by a wall portion 84, 86, respectively, having two layers wherein the first layer is formed of the sac 18, 38, respectively, and the second layer is formed of the housing 12a, 12c, respectively. Due to the materials of which the sacs 18, 38 and the housing 12a, 12c are formed, which may include for example, polyurethane for the sacs 18, 38 and titanium for the housing 12a, 12c, the wall portions 84, 86 are opaque such that the interior of the chambers 80, 82 cannot be viewed through the wall portions 84, 86.

Before implantation, each of the pumping chambers 80, 82 is devoid of liquid and it is only after the artificial heart 10 has been implanted that the pumping chambers 80, 82 are filled with blood which may enter the chambers 80, 82 via the blood inlets 26, 46, respectively. The blood entering each of the chambers 80, 82 displaces a quantity of gas, such as air, disposed within each of the chambers 80, 82 causing most of this air to exit the chambers 80, 82 through the blood outlets 20, 40, respectively. However, some of the air becomes entrapped in an elevated portion 88, 90 of each of the chambers 80, 82, respectively. Each of the elevated portions 88, 90 of the chambers 80, 82 is defined herein to include a portion of the volume of space located within each of the chambers 80, 82 that is elevated with respect to the remainder of the space located within the chambers 80, 82.

As described above, when implanted into a recipient lying on his back on the operating table 78, the artificial heart 10 will generally occupy the position shown in FIG. 2 wherein the center line 11 of the artificial heart 10 is perpendicular to the operating table 78. When the artificial heart 10 is positioned in this manner, the blood inlets 26, 46 and blood outlets 20, 40 are positioned below the pumping chambers 80, 82 and the elevated portions 88, 90 will generally occupy the positions shown in FIG. 2.

However, the position at which each of the elevated portions 88, 90 is located is dependent on the manner in which the artificial heart 10, and, more particularly, the pumping chambers 80, 82 are positioned within the recipient. As a result, the positions of the elevated portions 88, 90 are not fixed but will vary with each implantation procedure.

For example, in some instances the implanted artificial heart 10 may be tilted or otherwise offset from the perpendicular position of FIG. 2, which will generally cause the elevated portions 88, 90 to also be offset from the positions occupied by the elevated portions 88, 90 in FIG. 2. However, the positions at which the elevated portions 88, 90 are located always coincide with the positions at which the pockets of entrapped air 96, 98 are located, and the pockets of entrapped air 96, 98 are always. located adjacent to inner surfaces 92, 94, respectively, of the wall portions 84, 86, respectively. Thus, the pockets of entrapped air 96, 98 that form in the chambers 80, 82 are located at the elevated portions 88, 90, respectively, of the chambers 80, 82, which are adjacent to the inner surfaces 92, 94,,respectively, of the wall portions 84, 86, respectively.

Catheter

Figure 3:
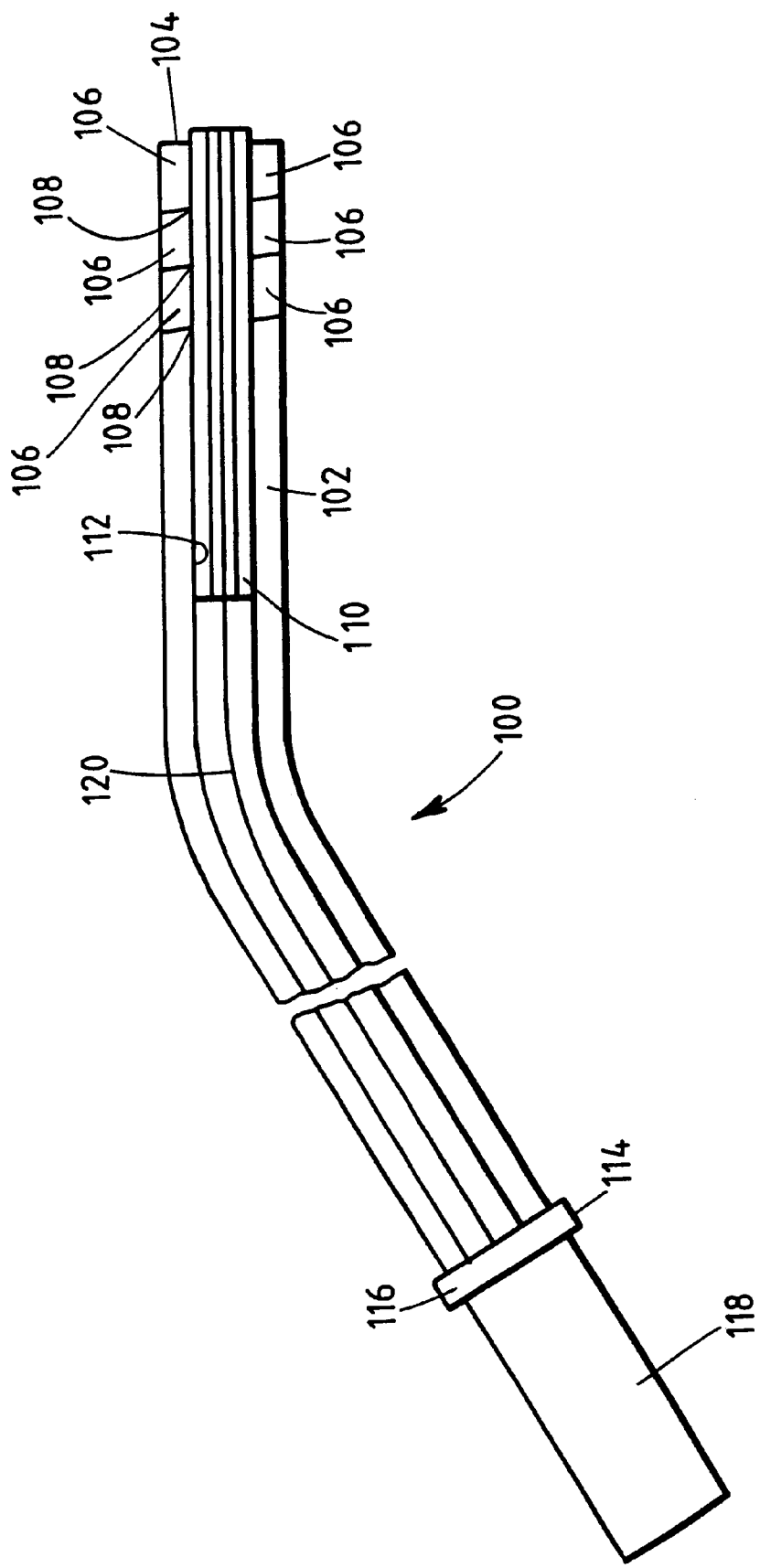
FIG. 3 illustrates a catheter, portions of which are shown in cross section, having a first material disposed on a first end of the catheter and having a vacuum generator disposed on a second end of the catheter in accordance with one embodiment of the present invention.

One embodiment of a catheter 100 that may be used to withdraw entrapped air from the implanted artificial heart 10 is shown in FIG. 3. Referring to FIG. 3, the catheter 100 may be formed of a flexible, silicone rubber tube 102 that includes a first end 104 at which a first material that generates a first magnetic field, $\vec{M}_1$, is disposed in a manner such that the direction of $\vec{M}_1$ is oriented along the longitudinal axis of the catheter 100. The first material may be embodied as a set of three ring-shaped magnets 106, comprising, for example, Samarium Cobalt 26 Mega Oersteds, that are disposed side by side. A set of orifices 108, one of which is disposed in the center of each ring-shaped magnet 106, are aligned to allow passage of a tube 110 therethrough. The magnets 106 may be bonded to the tube 110, and the tube 110, which is partially inserted into the catheter tube 102, may be bonded to an interior surface 112 of the catheter tube 102, to prevent the tube 110, from becoming dislodged therefrom.

At a second end 114 of the catheter 100, a standard luer lock 116, or other standard adaptor, may be disposed so that the catheter 100 may be attached to a vacuum generator 118 which may take the form of, for example, a stopcock and a syringe. The tube 102 may be dimensioned to allow passage of a guidewire 120 therethrough to facilitate positioning the catheter 100 within the pumping chambers 80, 82, as is described below.

Probe

Figure 4:
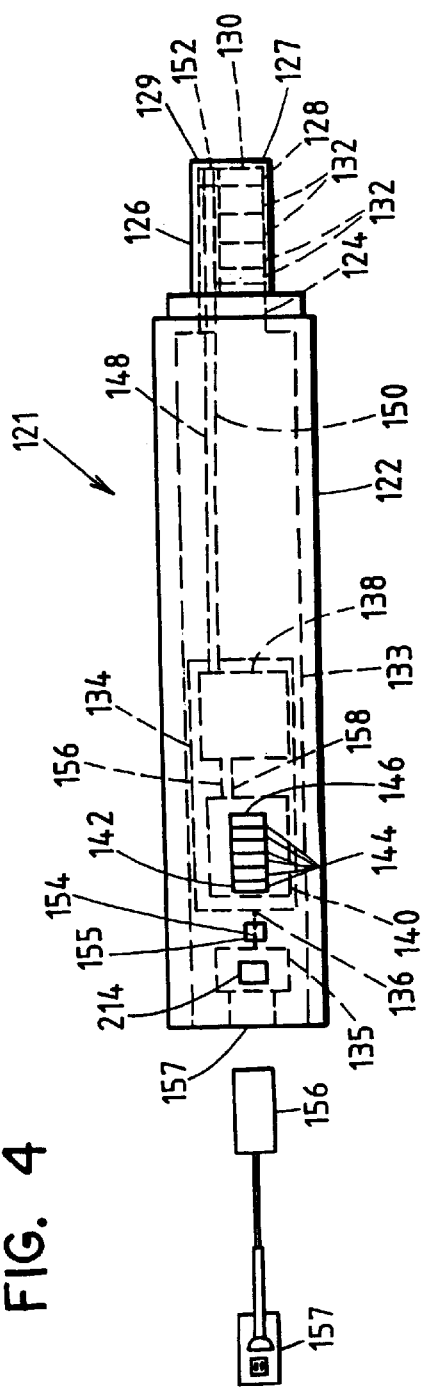
FIG. 4 illustrates a side view of a probe having a second material and a Hall-effect sensor coupled to an electronic circuit that is further coupled to an indicator in accordance with one embodiment of the present invention.
Figure 5:
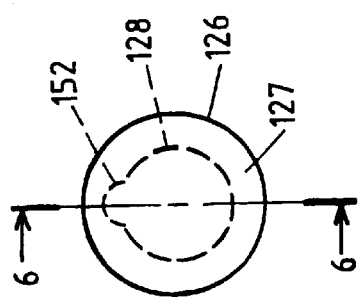
FIG. 5 illustrates a side view of a cylindrical tube that extends from the probe of FIG. 4.
Figure 6:
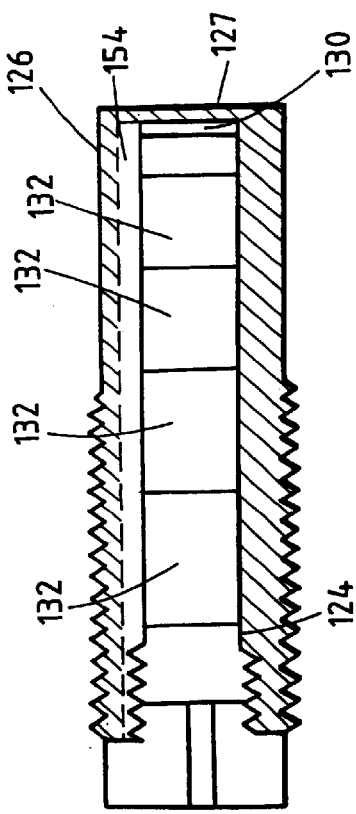
FIG. 6 illustrates a cross-sectional view of the cylindrical tube of FIG. 5 shown generally along view lines 6—6 of FIG. 5.

One embodiment of a probe 121 that may be used to guide the catheter tip 104 to the pocket of air 96 or 98 is shown in FIG. 4. Referring now to FIGS. 4, 5 and 6, the probe 121 includes a plastic housing 122 shaped in the form of an elongate shaft. The housing 122 includes a threaded, cylindrical bore 124 in which a threaded, cylindrical tube 126 is secured. The. cylindrical tube 126 is formed of a non-ferrous material, such as, for example, titanium, and includes an interior cavity 128 in which a Hall-effect sensor 130 is disposed. A second material that generates a second magnetic field, $\vec{M}_2$, is also disposed within the cavity 128 and is positioned such that $\vec{M}_2$ generates an attractive force that is aligned with the longitudinal axis of the cylindrical tube 126. The second material may be embodied as a set of disc-shaped magnets 132, comprising, for example, Neodymium Iron 35 Mega Oersted magnets, and are positioned in a stacked manner beside the Hall-effect sensor 130 which is disposed near an end 127 of. the cylindrical tube 126, hereinafter referred to as the probe tip 127.

Figure 7:
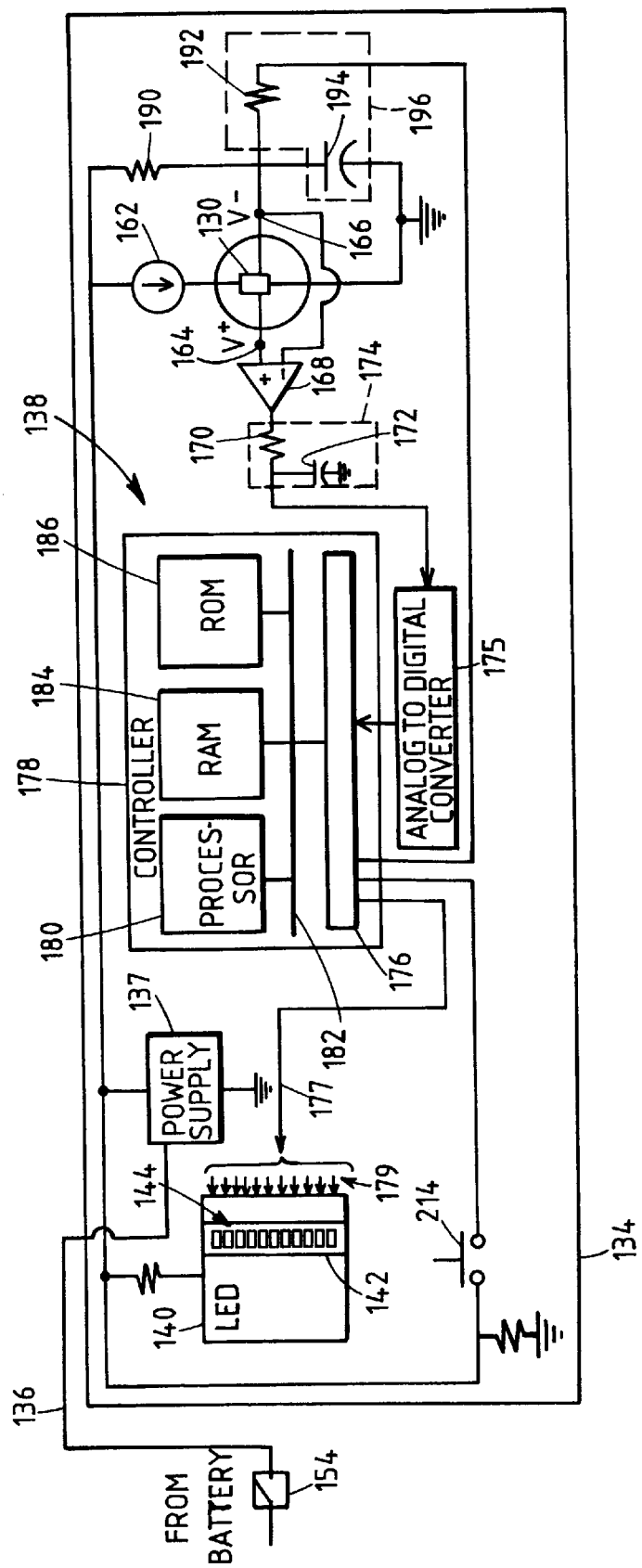
FIG. 7 is a circuit diagram that illustrates the components of the electronic circuit and the indicator in accordance with one embodiment of the present invention.

The plastic housing 122 further includes an interior cavity 133 within which an printed circuit board 134 and a battery 135 are disposed. The battery 135, which may be, for example, a nine volt battery, supplies power via a lead 136 to a power supply 137 (see FIG. 7) mounted on the printed circuit board 134. The power supply 137 converts the nine volt signal supplied by the battery 135 to a five volt signal and supplies the regulated five volt signal to the components disposed on the printed circuit board 134 including, an electronic circuit 138 and an indicator 140, such as a light emitting diode (LED) display device. The indicator 140 includes a display 142 that may be used to indicate distance and that may include, for example, a bar graph display having a plurality of N LED segments 144, each of which is defined to indicate a measurement corresponding to a predetermined distance such as, for example, one millimeter (mm). For illustrative purposes N is equal to eleven such that the LED display 142 has eleven LED segments 144. The indicator 140 is positioned in the cavity 133 such that the display 142 may be visually inspected by an operator through a first opening 146 that may be covered with, for example, a clear panel. To provide access to the interior cavity 133 and thereby allow for maintenance or repair of the components residing therein, the plastic housing 122 may be formed of two halves secured together with a set of screws (not shown) such that access to the interior cavity 133 may be had by loosening the screws and separating the halves.

A set of leads 148 by which power is supplied from the printed circuit board 134 to the Hall-effect sensor 130 and a set of leads 150 by which a proximity signal is supplied from the Hall-effect sensor 130 to the electronic circuit 138 are disposed in a channel 152 formed by a groove cut into the side of the interior cavity 128. A switch 154 also disposed in the interior cavity 133 of the housing 122 and extending through a second opening 155 may be used to control the flow of power from the battery 135 to the power supply 137 and the components supplied power thereby. Alternatively, and because it is difficult to sterilize batteries for surgical usage without causing damage thereto, the probe 121 may be adapted to connect to an electrical adaptor 156 that connects the probe 121 to a power source, such as an electrical outlet 157 (see FIG. 4), that is located externally to the probe 121. To enable usage of the electrical adaptor 156, the probe housing 122 may further include a third opening such as a power input port 157 into which the electrical adaptor 156 is inserted and which may have a lead connected thereto for delivering power to the power supply 137 thereby energizing the electronic circuit 138, the LED 140 and the Hall-effect sensor 130.

Controller

The electronic circuit 138 includes a controller 178 that converts the proximity signal generated by the Hall-effect sensor 130 to an indication signal for display by the indicator 140. More particularly, and referring now to FIG. 7 which comprises a schematic diagram of the components disposed on the printed circuit board 134, when exposed to a magnetic field, the Hall-effect sensor 130, which is energized by a constant current source 162, generates a voltage, $V_{HS}$, that is related to the cumulative strengths of the magnetic field(s), i.e., the magnetic flux density of the magnetic field(s), to which the Hall-effect sensor 130 is exposed. The voltage $V_{HS}$, which appears across a set of terminals 164 and 166, is amplified at an amplifier 168 and the amplified voltage is then filtered by a resistor 170 and a capacitor 172 configured to operate as a first low pass filter 174. The voltage filtered by the first low pass filter 174 is then delivered to an analog to digital converter ("A/D converter") 175 which converts the analog voltage signal to a digital value. The digital value is then supplied to an input/output bus 176 of the controller 178, which may be, for example, a single-chip microprocessor. The input/output bus 176 supplies the digital value to a processor 180 via a data communication bus 182 which enables communication between the devices connected thereto including the input/output bus 176, the processor 180 and one or more memory device(s), such as a random access memory (RAM) 184 and a read only memory 186. The processor 180 uses the digital value to access a look-up table 200 (see FIG. 9A) stored in the ROM 186 for the purpose of identifying an appropriate one of the LED segments for actuation. After the appropriate LED segment has been identified, the processor 180 generates an LED segment actuation signal which is subsequently transmitted via the input/output bus 176 to one of a set of LED inputs 179, wherein the set of inputs 179 contains N inputs and wherein each input 179 corresponds to the actuation of one of the N segments 144 of the LED display 142. It should be understood that the input/output bus 176 of the controller is configured to include a set of N output pins 177 that are connected to the N inputs 179 of the LED 140. of course, the output pins 177, although represented in FIG. 7 by a single output line, actually includes a set of N output lines.

A bias voltage, $V_{BIAS}$, is applied to the terminal 166 by delivering a DC voltage signal dropped across a resistor 190 to the terminal 166 and by further delivering a filtered pulse-width modulated signal generated by the processor 180 to the terminal 166. The pulse width modulated signal is filtered by a resistor 192 and a capacitor 194 configured to operate as a second low pass filter 196. The magnitude of the bias voltage, $V_{BIAS}$, is selected to offset the effects of the magnetic field $\vec{M}_2$ (generated by the probe magnets 132) on the voltage, $V_{HS}$ (generated by the Hall-effect sensor 130). More particularly, as stated hereinbefore, and in accordance with conventional Hall-effect sensor operation, the voltage $V_{HS}$ generated by the Hall-effect sensor 130 is related to the cumulative strengths of the magnetic fields to which the Hall-effect sensor 130 is exposed. Therefore, assuming that the Hall-effect sensor 130 is exposed to the magnetic fields $\vec{M}_1$ and $\vec{M}_2$ and further assuming that the bias voltage, $V_{BIAS}$ is not applied to the terminal 166, then the voltage, $V_{HS}$, generated by the Hall-effect sensor 130 is due, in part, to a voltage $V_1$, that is generated in response to $\vec{M}_1$, and, in part, to a voltage $V_2$ that is generated in response to $\vec{M}_2$. Moreover, because the strengths of the magnetic fields $\vec{M}_1$ and $\vec{M}_2$ are cumulative, the voltages $V_1$ and $V_2$ are also cumulative such that:

$$V_{HS}=V_1+V_2 \tag{1}$$

In addition, the strengths of $\vec{M}_1$ and $\vec{M}_2$, as measured by the Hall-effect sensor 130, and thus the voltages $V_1$ and $V_2$, are related to the distances between the sources of the magnetic fields and the Hall-effect sensor 130. As a result, the voltage $V_1$ varies with the distance between the Hall-effect sensor 130 disposed on the probe tip 127 and the magnets 106 disposed on the catheter tip 104. Thus, provided that the relationship between the magnitude of $V_1$ and the distance between the catheter tip 104 and the probe tip 127 is known, the voltage $V_1$ may be used to determine the distance between the catheter tip 104 and the probe tip 127. To obtain the voltage signal, $V_1$, so that it may be used in this manner, the portion of the voltage signal, $V_{HS}$, that is contributed by the voltage $V_2$ is offset such that the voltage, $V_{HS}$, is equal to the voltage $V_1$. This is achieved by applying the bias voltage, $V_{BIAS}$, to the terminal 166 and ensuring that the bias voltage is set at a level that is equal in magnitude and opposite in direction to the voltage $V_2$ thereby causing the voltage $V_2$ to be deducted from the voltage $V_{HS}$ as follows:

$$V_{HS}=(V_1+V_2)-V_2=V_1 \tag{2}$$

It should be noted that, because the magnets 132 disposed on the probe 121 do not move relative to the Hall-effect sensor 130 which is also disposed on the probe 121, $V_2$ and, thus, $V_{BIAS}$, are constant voltages.

It should further be noted that the magnitude of the signal of interest, i.e., the portion of the voltage signal, $V_{HS}$, due to the magnitude of $\vec{M}_1$, as measured by the Hall-effect sensor 130, is small relative to the portion of the voltage signal, $V_{HS}$, due to the magnitude of $\vec{M}_2$. Moreover, the Hall-effect sensor 130 is sized to accurately measure signals in the range expected for $\vec{M}_1$ and, therefore, if the bias voltage, $V_{BIAS}$, Is not applied to the terminal 166 of the Hall-effect sensor 130, the portion of the voltage signal, $V_{HS}$, due to the magnetic field, $\vec{M}_2$, may cause the Hall-effect sensor 130 to saturate. Saturation of the Hall-effect sensor yields the signal of interest unrecoverable. As a result, other methods of accounting for the bias voltage, such as, for example, leaving the voltage signal, $V_{HS}$, unbiased at the Hall-effect sensor 130 and instead using the processor 180 to Stab/deduct the digital equivalent of the bias voltage from the unbiased voltage signal are likely to result in the loss of the signal of interest. Thus, the applying the bias voltage, $V_{BIAS}$, to the terminal 166 prevents the Hall-effect 130 sensor from saturating thereby enabling the measurement of the signal of interest.

Operation

Figure 8:
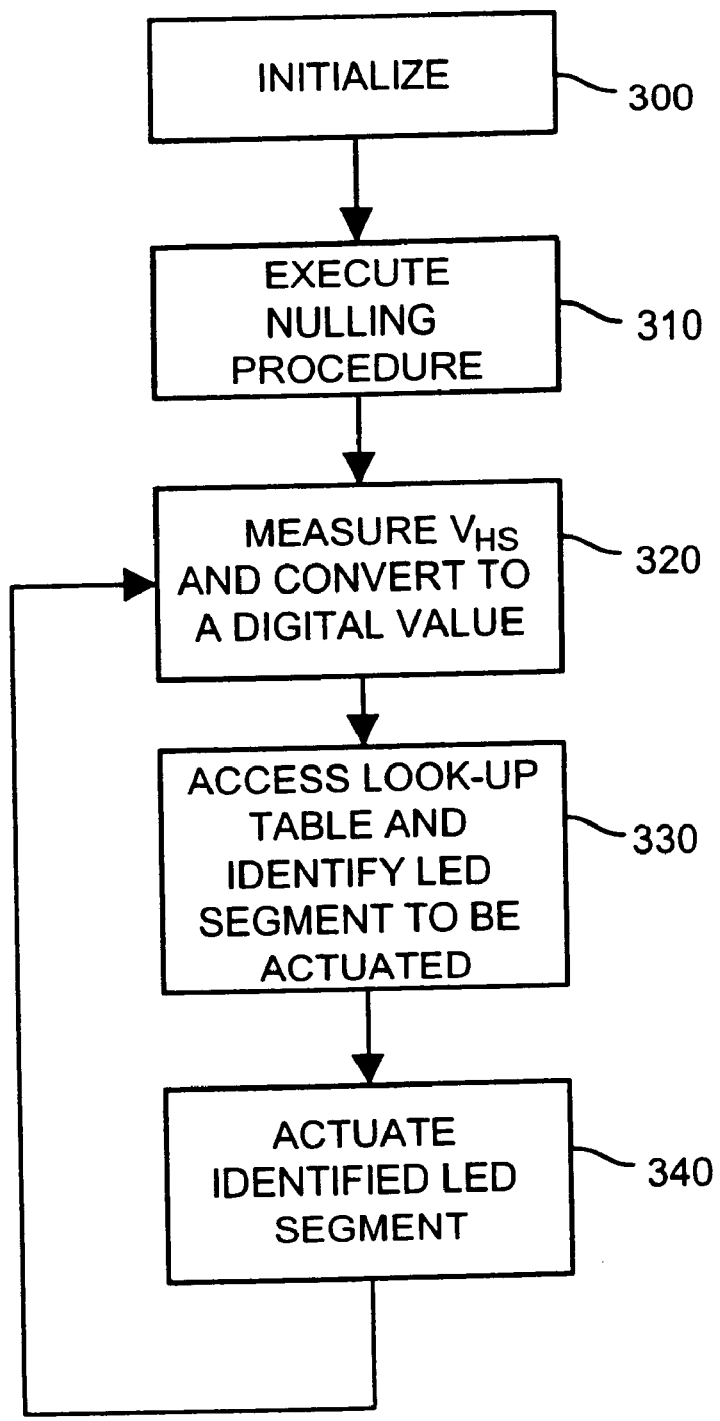
FIG. 8 is a flow chart that illustrates the steps of a method by which the probe measures the distance between the tip of the catheter and the probe tip.

Referring now to FIG. 8, a method by which the probe measures and indicates the distance between the probe tip 127 and the catheter tip 104 begins at step 300 where the method is initialized. It should be understood that the steps of the method initialized at the step 300 may be performed using a software routine stored in a program memory such as the ROM 186. The step of initializing performed by the processor 180 may include locating the software routine in the memory 186 and initializing registers internal to the processor 180 as may be necessary to execute the software.

Figures 9A, 9B, 11:
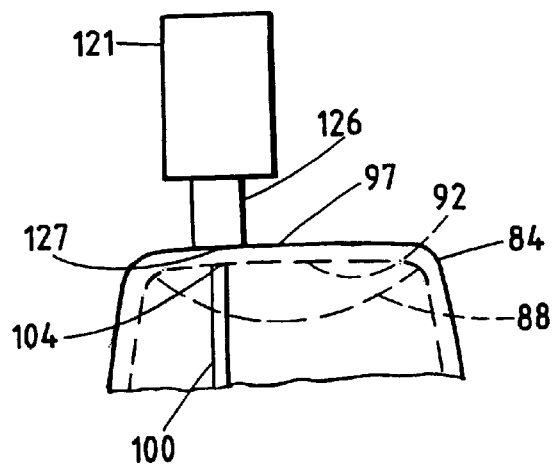
FIG. 9A illustrates a look-up table containing voltage values that may be used to actuate the indicator in accordance with one embodiment of the present invention.
FIG. 9B illustrates a set of analog voltage values that may be used determine the voltage values that are entered into the look-up table of FIG. 9A.
FIG. 11 illustrates the positions occupied by the catheter tip and the probe tip relative to one another and relative to the wall portion of the pumping chamber when the probe tip has magnetically captured the catheter tip.

Next, at step 310 a nulling procedure is executed during which the bias voltage, $V_{BIAS}$, applied to the terminal 166 is adjusted to a level necessary to offset the voltage, $V_2$. The nulling procedure performed at the step 310 is described in further detail with reference to FIG. 10. After the nulling procedure has been performed, the program continues at step 320 where the voltage signal generated by the Hall-effect sensor 130, $V_{HS}$, and converted by the A/D converter 175 is measured by the processor 180. Next, at step 330, the processor 180 uses the measured value of $V_{HS}$ to access the look-up table 200 (see FIG. 9A) stored in the ROM 186 (see FIG. 7). More particularly, and referring also to FIGS. 9A and 9B, the look-up table 200 may include a first column 202 and a second column 204 each having N rows wherein, as defined above, N equals the number of segments 144 in the LED display 142, i.e., eleven segments. The first column 202 contains a set of numbers ranging from one through n, each of which identifies a corresponding one of the LED segments, i.e., the row having the number one corresponds to the first LED segment and the row having the number two corresponds to the second LED segment, etc. To enable the display of distances ranging from one to N millimeters, the first LED segment is assigned to represent a distance of N–0 millimeters and the second LED segment is assigned to represent a distance of N–1 millimeters, etc. The second column 204 contains digital values that are obtained by measuring a set of analog voltages 201 (See FIG. 9B) generated by the Hall-effect sensor 130 and by converting the measured analog voltages into digital values. More particularly, the probe tip 127 is placed at a set of discrete distances from the catheter tip 104, wherein each of the discrete distances is equal to one of the distances represented by the LED segments 144. At each distance, the analog voltage 201 generated by the Hall-effect sensor 130 is measured at the output of the amplifier 168 using a voltmeter (not shown) and is then converted to a digital value. The digital value obtained for each discrete distance is then entered into the row corresponding to the LED segment that represents the discrete distance. It should be noted that the values provided in the look-up table of FIG. 9A and the set of analog voltage values provided in FIG. 9B are intended to be exemplary only.

It should be further noted that, although the look-up table data obtained in the manner described is useful for indicating the distance between the catheter tip 104 and the probe tip 127, the data entered into the look-up table 200 could instead be obtained such that the distance indicated by the LED display 142 reflects the distance between the Hall-effect sensor 130 and the catheter tip 104. The distance between the Hall-effect sensor 130 and the catheter tip 104 is slightly greater than the distance between the probe tip 127 and the catheter tip 104 because the Hall-effect sensor 130 is offset a short distance from the probe tip 127. Of course, to obtain data that may be used to indicate the distance between the Hall-effect sensor 130 and the catheter tip 104, the distance between the Hall-effect sensor 130 and the probe tip 127 must be known and must be accounted for when placing the probe tip 127 near the catheter tip 104 for the purpose of obtaining the data. For example, assuming that the distance between the Hall-effect sensor 130 and the probe tip 127 is one half of a millimeter (0.05 mm) then, to obtain data that reflects a distance of one millimeter between the Hall-effect sensor 130 and the catheter tip 104, the probe tip 127 need only be placed a distance of one half of a millimeter from the catheter tip 104.

The step of accessing the look-up table 200 performed by the processor 180 at step 330 may include the step of comparing the digital value obtained at step 320 to each of the values in the second column 204 and, based on the comparison, the processor 180 may actuate an appropriate one of the LED segments. For example, the processor 180 may be programmed to compare the digital value converted by the A/D converter 175 to the digital value in the first row of the second column 204. If the digital value converted by the A/D converter 175 is less than the digital value in the first row of the second column 204, then the processor 180 may actuate the first LED segment thereby to indicate that the probe tip 127 is located a distance greater than N (or 11) millimeters from the catheter tip 104. If the digital value converted by the A/D converter 175 is not less than the digital value in the first row of the second column 204, then the processor 180 may compare the digital value converted by the A/D converter 175 to the digital value in the second row of the second column 204. If the digital value converted by the A/D converter 175 is less than the digital value in the second row of the second column 204, but greater than or equal to the digital value in the first row of the second column 204, then the processor 180 may actuate the second LED segment thereby to indicate that the probe tip is located at a distance between N and N–1 (11 and 10) millimeters from the catheter tip 104. The processor 180 may be programmed to continue in this manner until the processor 180 has identified an appropriate one of the LED segments 144 to be actuated. The appropriate LED segment 144 is then actuated via an actuation signal sent from the processor 180 to an input 179 of the LED 140 that is associated with the appropriate LED segment 144, thereby to actuate the LED segment, at step 340. After step 340, the program loops back to step 320 and the program continues to loop through the steps 320 through 340 until a halt signal is generated which may occur, for example, when the electronic circuit 138 is de-energized, i.e., the switch 154 is turned off or the adapter 156 is unplugged from the outlet 157.

Nulling Procedure

Figure 10:
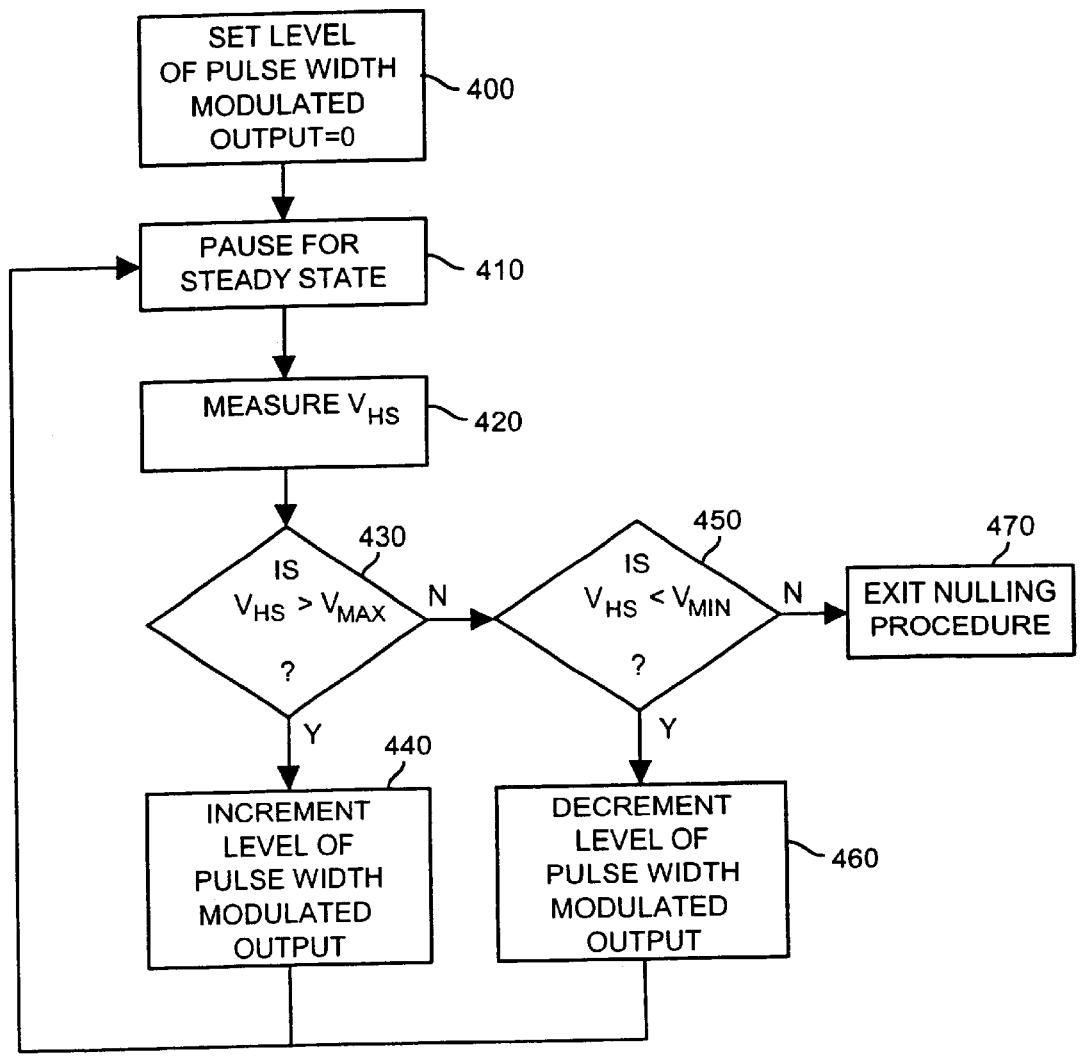
FIG. 10 is a flow chart that illustrates the steps of a method for executing a nulling procedure so that the second material does not affect the accuracy of the probe measurements.

Referring now to FIG. 10, as stated hereinbefore, the nulling procedure performed at the step 310 (see FIG. 8), involves adjusting the bias voltage, $V_{BIAS}$, applied to the terminal 166 to a level necessary to offset the voltage $V_2$. Before the nulling procedure is executed, the probe operator (not shown) ensures that the voltage $V_1$ is equal to zero by placing the probe 121 a distance from the catheter 100 sufficient to prohibit the magnets 106 disposed on the catheter 100 from affecting the magnitude of $V_{HS}$. Likewise, the operator also ensures that the probe 121 is not located near any other magnetic materials that may adversely affect the magnitude of $V_{HS}$ during execution of the nulling procedure.

Referring to Eq. 1, if the voltage $V_1$ is set equal to zero, and assuming that no other magnetic materials are near enough to affect the probe measurements, then the voltage $V_{HS}$ is equal to the voltage $V_2$. When the bias voltage, $V_{BIAS}$ is applied at the terminal 166, the voltage, $V_{HS}$, is affected as follows:

$$V_{HS} = V_2 V_{BIAS}. \tag{3}$$

Thus, to offset $V_2$, $V_{BIAS}$ is adjusted until the magnitude of $V_{BIAS}$ is approximately equal to $V_2$ such that $V_{HS}$ is approximately equal to zero. Note, however, that instead of applying a bias voltage, $V_{BIAS}$, that causes $V_{HS}$ to be approximately equal to zero, the bias voltage, $V_{BIAS}$, may instead be set to a value that is within a voltage band bounded by a minimum voltage, $V_{min}$, and a maximum voltage, $V_{max}$ wherein both $V_{min}$ and $V_{max}$ are positive values. By adjusting $V_{BIAS}$ until $V_{HS}$ is within the voltage band, the operator is assured that the voltage value for $V_{HS}$ remains positive even after the bias voltage, $V_{BIAS}$, has been applied to the terminal 166. Such a voltage band may be used, for example, in an embodiment, such as that shown in FIG. 7, wherein the electronic circuit 138 is configured so that negative voltages cannot be generated at the output of the amplifier 168. For a configuration wherein negative voltages cannot be generated at the output of the amplifier 168, during the process of adjusting $V_{BIAS}$ until $V_{HS}$ is approximately zero, $V_{BIAS}$ may be set at a value that is too large, causing $V_{HS}$ to be significantly less than zero and potentially having significant adverse effects on the accuracy of the probe 121 measurements. However, because negative voltages do not appear at the output of the amplifier 168, the operator would be unable to detect that $V_{HS}$ is actually significantly less than zero. Thus, by setting $V_{HS}$ to a positive value after the bias voltage, $V_{BIAS}$, has been applied, the situation wherein $V_{BIAS}$ is set to a value such that $V_{HS}$ is significantly less than zero is avoided.

More particularly, the nulling procedure 310 begins at step 400 wherein the processor 180 sets the level of the pulse width modulated signal to zero such that $V_{BIAS}=0$. Thereafter, the program continues at step 410 wherein the processor 180 waits an amount of time sufficient to allow the signal output by the first low pass filter 174 to reach steady state. After steady state has been achieved, at step 420, the processor 180 measures the value of $V_{HS}$. The program then continues at step 430 wherein the processor 180 tests whether $V_{HS}$ is greater than the maximum voltage, $V_{max}$. If $V_{HS}$ is greater than $V_{max}$, then the program continues at step 440 wherein the processor 180 increments the level of the pulse width modulated signal which causes $V_{HS}$ to decrease. After incrementing the pulse width modulated signal, the program loops back to step 410 wherein the processor 180 again waits an amount of time sufficient to allow for the signal output by the first low pass filter 174 to reach steady state and then the program continues at step 420 and steps subsequent thereto as described below.

If, at step 430, $V_{HS}$ is not greater than $V_{max}$, then the program continues at step 450 wherein the processor 180 tests whether $V_{HS}$ is less than the minimum voltage, $V_{min}$. If $V_{HS}$ is less than $V_{min}$, then the program continues at step 460 where the processor 180 decrements the level of the pulse width modulated signal which causes $V_{HS}$ to increase. After decrementing the pulse width modulated signal, the program loops back to step 410 and steps subsequent thereto. If instead, at step 450, $V_{HS}$ is not less than the voltage $V_{min}$ thereby indicating that $V_{HS}$ lies within the voltage band bounded by $V_{min}$ and $V_{max}$, then the nulling procedure is exited at step 470 and the program returns to step 220 (see FIG. 8). Of course, if such a voltage band is used in the nulling procedure, then the values entered into the look-up table 200 (see FIG. 9A) must be selected such that the value at which $V_{HS}$ is set during the steps of the nulling procedure, when converted to a digital value, correspond to a voltage value that will actuate only the first of the LED segments 144 on the LED display 142. For example, assuming that the digital value corresponding to the largest distance displayable on the LED 140 is actuated when the LED 140 receives a digital value of between zero and 41, then $V_{min}$ and $V_{max}$ may be set at digital voltages that are less than 42, such as $V_{min}=10$ and $V_{max}=40$. Of course, it should be understood that these voltage values are intended to be exemplary only and it should further be understood that the actual values selected to represent the minimum and maximum bounds of the voltage band may be dependent upon the type of indicator 140 used.

The nulling procedure, in addition to being automatically initiated upon energizing the electronic circuit 138 at step 300, may also be manually initiated by pressing an interrupt switch 214 (see FIG. 7) which causes the processor 180 to execute the nulling procedure depicted in the flow chart of FIG. 10. This interrupt switch 214 may be used, for example, when the bias voltage, $V_{BIAS}$, has drifted outside of the voltage band bounded by $V_{min}$ and $V_{max}$.

Method of Removing Pocket of Air from Blood Pump

Referring now to FIG. 11, a method for using the catheter 100 and the probe 121 to remove the pocket of air 96 from the interior of the pumping chamber 80 may be performed by an operator, such as a surgeon, who begins the method by inserting the guidewire 120 into the catheter tube 102 and then using the guidewire 120 to insert a predetermined length of the catheter tube 102 into the pumping chamber 80 via the blood inlet 26. Of course, it is assumed that when the step of inserting the catheter tube 102 is performed, the artificial heart 10 has already been inserted into the chest cavity of the recipient who is lying on the operating table 78. It is further assumed that the pumping chamber 80 has already been filled with blood and that a pocket of air 96 has become entrapped in the elevated portion 88 of the pumping chamber 80. The pre-determined length of catheter tube 102 inserted using the guidewire 120 is preferably chosen such that, after insertion, the catheter tip 104 is located at a position inside of the chamber 80 that is close to the elevated portion 88 of the chamber 80. As described with respect to FIG. 2, the position of the elevated portion 88 is not fixed relative to the structure of the artificial heart 10 but instead may vary with each implantation. However, the surgeon performing the implantation procedure will be able to determine the location of the elevated portion 88 by visually inspecting the implanted artificial heart 10 and finding the portion of the pumping chamber 80 that is most elevated.

After the catheter tube 102 has been inserted, the surgeon places the probe tip 127 in contact with, and adjacent to, an outer surface 97 of the wall portion 84. The surgeon then moves the probe tip 127 about the outer surface 97 of the wall portion 84 until the LED display 142 indicates that the distance between the probe tip 127 and the catheter tip 104 is equal to or nearly equal to the thickness of the wall portion 84. Of course, it is assumed that the thickness of the wall portion 84 is known and, preferably, that the thickness of the wall portion 84 equals the distance represented by one or more of the LED segments 144. For example, if the thickness of the wall portion 84 is one millimeter, then the probe 121 is moved about the exterior surface 97 of the wall portion 84 until the LED segment 144 corresponding to a distance of one millimeter lights up.

When the LED display 142 indicates that the catheter tip 104 and the probe tip 127 are separated by the thickness of the wall portion 84, the probe tip 127 is assumed to have magnetically captured the catheter tip 104 such that the catheter tip 104, located adjacent to the inner surface 92, and the probe tip 127, located adjacent to the outer surface 97, are aligned with one another in the manner depicted in FIG. 11. When the probe tip 127 and the catheter tip 104 are aligned in this manner, the force of the magnetic attraction between the catheter tip 104 and the probe tip 127 causes the catheter tip 104 to follow the movement of the probe tip 127 such that the probe tip 127 may be used to guide the catheter tip 104 to the elevated portion 88.

Once the catheter tip 104 has been magnetically captured, the surgeon removes the guidewire 120 from the catheter tube 102. Next, the surgeon moves the probe tip 127 to a position on the outer surface 97 of the wall portion 84 such that the catheter tip 104 is guided to the elevated portion 88 and is located inside the pocket of air 96. After the surgeon has positioned the catheter tip 104 within the pocket of air 96, the surgeon uses the vacuum generator 118 located on the distal end of the catheter tube 102 to suction the pocket of air 96 from the pumping chamber 80. After the suctioning has been performed, the method is complete.

Certain modifications to the present invention may occur to one of ordinary skill in the art. For example, although the first and the second materials may be implemented with a plurality of magnets, as described herein, the first and/or the second materials may instead be implemented with a steel rod having a wire with electrical current flowing therethrough wrapped around the steel rod, thereby to generate the second magnetic field, $\vec{M}_2$. As a further example, provided that at least one of the first material or the second material is embodied using a magnetic material, the other of the first material or the second material may instead be implemented with a ferrous material having a high permeability. The placement of a ferrous material near a magnet causes the flux lines of the magnetic field associated with the magnet to constrict, thereby causing an increase in the magnetic flux density in the region of the constricted lines. This increase is measurable by the Hall-effect sensor 130 and thus, only one of the first and second materials need be embodied using a magnetic material. Of course, it will be understood that if such a ferrous material is used instead of the magnets described herein, the strength of the magnetic force between the probe tip 127 and catheter-tip 104 will likely be reduced and, as a result, the strength/magnitude of the voltage signal, $V_{HS}$, responsive to the magnetic force is also reduced. It will further be understood by one of ordinary skill in the art that the application of a bias voltage, $V_{BIAS}$, may not be necessary if the second material is formed of a ferrous material instead of a set of magnets.

In addition, the magnetic flux density of the first material and/or the second material must be of a sufficient magnitude to enable attraction of the catheter tip 104 to the probe tip 127 through the wall portion 84 and must further be of a sufficient magnitude to enable guidance of the catheter tip 104 to the pocket of air 96 using the probe tip 127.

Moreover, the first material disposed at the tip of the catheter 100 may be positioned such that the magnetic field generated thereby is oriented radially instead of axially. Such a configuration will facilitate guiding the catheter 100 through a passage, such as a blood vessel.

Further, the indicator 140 is not limited to an LED device as described herein, but may instead be implemented using any type of visual indicator or may instead be implemented using an audible indicator that, for example, uses beeps or tones to indicate the proximity of the probe tip 127 to the catheter tip 104.

Further still, the controller 178 may be implemented using a microprocessor chip or may instead by implemented with a micro-controller having analog-to-digital conversion capabilities. Indeed, controller 178 may be implemented with any device capable of receiving the measured value of the voltage, $V_{HS}$, and then supplying an appropriate actuation signal to the indicator in response thereto.

Thus, while the present invention has been described with reference to specific examples, these examples are to be construed as illustrative only, and are provided for the purpose of teaching those skilled in the art the best mode of carrying out the invention. The details of the structure and method may be varied substantially without departing from the spirit of the invention, and the exclusive use of all modifications which come within the scope of the appended claims is reserved.

What is claimed is:

1. A system for removing a pocket of gas from a blood pump, comprising:

a blood pump having a wall portion formed of a non-ferrous material, said wall portion having a thickness and having an inner surface and an outer surface, wherein said wall portion is opaque, said blood pump further having a chamber disposed therein, wherein said chamber is at least partially defined by said wall portion, and wherein said pocket of gas is located at a position that is adjacent to said inner surface of said wall portion;

a catheter having a first end and a second end, said first end having a first magnet disposed adjacent thereto, wherein said first magnet generates a first magnetic field, and wherein said first end of said catheter may be positioned inside of said chamber;

a vacuum generator coupled to said second end of said catheter, wherein said vacuum generator is adapted to remove said pocket of gas from said chamber when said first end of said catheter is disposed therein;

a positioning probe adapted to be held at a location outside of said chamber in order to position said first end of said catheter at said position where said pocket of gas is located so that said pocket of gas may be removed from said chamber;

a second magnet, said second magnet being disposed on said probe, wherein said second magnet generates a second magnetic field, wherein said first and second magnetic fields are of sufficient strength to cause said first magnet to be attracted to said second magnet through said wall portion of said chamber such that when said second magnet is disposed adjacent to said outer surface of said wall portion and said first magnet is disposed within said chamber, said first magnet moves toward said second magnet until said first magnet is aligned with said second magnet and said first magnet is disposed adjacent to said inner surface of said wall portion and said second magnet is disposed adjacent to said outer surface of said wall portion; and further wherein said first and second magnetic fields are of sufficient strength such that when said first magnet and said second magnet are aligned with each other and said first magnet is disposed adjacent to said inner surface of said wall portion and said second magnet is disposed adjacent to said outer surface of said wall portion, a movement of said second magnet causes said first magnet to follow said movement such that said second magnet may be used to guide said first magnet to said position where said pocket of gas is located;

a sensor disposed on said probe, wherein said sensor generates a proximity signal having a magnitude relating to a distance between said first magnet and said second magnet;

an electronic circuit operatively coupled to said sensor, wherein said electronic circuit generates an indicator signal in response to said proximity signal generated by said sensor;

an indicator operatively coupled to said electronic circuit that generates an indication based on said indicator signal generated by said electronic circuit, wherein said indicator may be used to indicate when said distance between said first and said second magnets is approximately equal to said thickness of said wall portion such that said first magnet is disposed adjacent to said inner surface of said wall portion and said second magnet is disposed adjacent to said outer surface of said wall portion and said first and second magnets are aligned with each other.

2. A system for removing a pocket of gas from a blood pump as defined in claim 1, wherein said magnitude of said proximity signal generated by said sensor is related to said distance between said first and said second magnets.

3. A system for removing a pocket of gas from a blood pump as defined in claim 1, wherein said sensor comprises a Hall-effect sensor.

4. A system for removing a pocket of gas from a blood pump as defined in claim 1, wherein said catheter comprises a flexible silicone rubber tube.

5. A system for removing a pocket of gas from a blood pump as defined in claim 1, additionally comprising a plurality of magnets, wherein said plurality of magnets are disposed on said first end of said catheter with said first magnet.

6. A system for removing a pocket of gas from a blood pump as defined in claim 5, wherein each of said plurality of magnets is shaped like a ring and wherein said plurality of magnets are stacked together and bonded to a tube and further wherein said tube is disposed within said first end of said catheter and is attached to said first end of said catheter.

7. A system for removing a pocket of gas from a blood pump as defined in claim 1, further comprising a wire that is removably disposed in said catheter, wherein said wire facilitates positioning of said catheter inside of said chamber.

8. A system for removing a pocket of gas from a blood pump as defined in claim 1, wherein said indicator comprises a light emitting diode.

9. A system for removing a pocket of gas from a blood pump as defined in claim 1, wherein said indicator comprises a plurality of visual indicators arranged in a bar graph configuration wherein each of said plurality of visual indicators represents a measure of distance such that said plurality of visual indicators represents a range of distance measurements.

10. A system for removing a pocket of gas from a blood pump as defined in claim 1, wherein said electronic circuit causes a bias voltage to be applied to said sensor thereby to offset an effect of said second magnet on said sensor.

11. A system for removing a pocket of gas from a blood pump, comprising:
   a blood pump having a wall portion with an inner surface and an outer surface, said blood pump having a chamber at least partially defined by said wall portion, said chamber of said blood pump having a pocket of gas disposed therein;
   a catheter having a first attractive material that generates a first attractive field;
   a vacuum generator coupled to said catheter, said vacuum generator being adapted to remove said pocket of gas from said chamber when a portion of said catheter is disposed therein;
   a positioning probe adapted to be disposed at a location outside of said chamber to allow said portion of said catheter to be positioned within said pocket of gas;
   a second attractive material associated with said probe, movement of said second attractive material causing movement of said first attractive material when said second attractive material is disposed outside said chamber and when said first attractive material is disposed within said chamber;
   a sensor associated with said probe, said sensor generating a proximity signal having a magnitude relating to a distance between said first attractive material and said second attractive material;
   an electronic circuit operatively coupled to said sensor, said electronic circuit generating an indicator signal in response to said proximity signal generated by said sensor; and
   an indicator operatively coupled to said electronic circuit, said indicator generating an indication based on said indicator signal generated by said electronic circuit, said indication relating to said distance between said first and second attractive materials.

12. A system for removing a pocket of gas from a blood pump as defined in claim 11 wherein said sensor comprises a Hall-effect sensor.

13. A system for removing a pocket of gas from a blood pump as defined in claim 11 wherein said first attractive material is attached to said catheter at a position adjacent a first end of said catheter.

14. A system for removing a pocket of gas from a blood pump as defined in claim 11 wherein said portion of said catheter comprises a first end of said catheter.

15. A system for removing a pocket of gas from a blood pump as defined in claim 11 wherein said catheter comprises a flexible silicone rubber tube.

16. A system for removing a pocket of gas from a blood pump as defined in claim 11 wherein said first attractive material comprises a magnet and wherein said second attractive material comprises a magnet.

17. A system for removing a pocket of gas from a blood pump as defined in claim 16, wherein each of said magnets is shaped like a ring.

18. A system for removing a pocket of gas from a blood pump as defined in claim 11 additionally comprising a wire that is removably disposed in said catheter to facilitate positioning of said catheter inside said chamber.

19. A system for removing a pocket of gas from a blood pump as defined in claim 11 wherein said indicator comprises a light-emitting diode.

20. A system for removing a pocket of gas from a blood pump as defined in claim 11 wherein said indicator comprises a plurality of visual indicators and wherein each of said visual indicators represents a measure of distance.

21. A method of removing gas from a pocket of gas disposed within a chamber of a blood pump using a catheter provided with a first material, said chamber of said blood pump being at least partially bounded by a wall portion, said pocket of gas being located adjacent an inner surface of said wall portion at least partially bounding said chamber of said blood pump, said method comprising:
   a) disposing said catheter in said chamber of said blood pump;
   b) disposing a probe having a second material that attracts said first material of said catheter at a position in which said wall portion at least partially bounding said chamber of said blood pump is disposed between said first material of said catheter and said probe;
   c) monitoring an indicator to determine if said second material of said probe has attracted said first material of said catheter to a position disposed adjacent said inner surface of said wall portion at least partially bounding said chamber of said blood pump;

d) moving said probe to cause said first material of said catheter to be moved so that said catheter is disposed in said pocket of gas; and (e) with said catheter disposed in said pocket of gas in said chamber of said blood pump, operating a vacuum generator to cause gas to be removed from said chamber of said blood pump.

22. A method as defined in claim 21 wherein said second attractive material comprises a magnetic material and wherein b) comprises disposing a probe having a magnet at said position in which said wall portion is disposed between said first material of said catheter and said probe.

23. A method as defined in claim 21 wherein said first attractive material comprises a magnetic material and wherein b) comprises disposing a probe having said second attractive material at said position in which said wall portion is disposed between a magnet attached to said catheter and said probe.

* * * * *

UNITED STATES PATENT AND TRADEMARK OFFICE
CERTIFICATE OF CORRECTION

PATENT NO. : 6,432,136 B1  Page 1 of 1
DATED : August 13, 2002
INVENTOR(S) : Weiss et al.

It is certified that error appears in the above-identified patent and that said Letters Patent is hereby corrected as shown below:

Column 3,
Line 5, please delete "used determine" and insert -- used to determine -- therefor.

Column 6,
Line 16, please delete "which an printed" and insert -- which a printed -- therefor.

Column 7,
Line 38, please delete "LED 140. of course," and insert -- LED 140. Of course, -- therefor.

Column 8,
Line 35, please delete "VBIAS, Is" and insert -- VBIAS, is -- therefor.
Line 43, please delete "Stab/".
Line 47, please delete "Hall-effect 130 sensor" and insert -- Hall-effect sensor 130 -- therefor.

Column 10,
Line 53, please delete "VHS = V2 VBIAS." and insert -- VHS = V2 - VBIAS. -- therefor.

Signed and Sealed this

Thirtieth Day of September, 2003

JAMES E. ROGAN
*Director of the United States Patent and Trademark Office*